United States Patent [19]

Meyer

[11] 4,432,886
[45] Feb. 21, 1984

[54] CATIONIC FLUORESCENT WHITENING AGENTS

[75] Inventor: Hans R. Meyer, Binningen, Switzerland

[73] Assignee: Ciba-Geigy Corporation, Ardsley, N.Y.

[21] Appl. No.: 421,201

[22] Filed: Sep. 22, 1982

Related U.S. Application Data

[62] Division of Ser. No. 200,738, Oct. 27, 1980, Pat. No. 4,384,121.

[30] Foreign Application Priority Data

Nov. 1, 1979 [CH] Switzerland .......................... 9808/79

[51] Int. Cl.$^3$ .................. C07D 405/04; C07D 413/02
[52] U.S. Cl. .................................... 252/301.27; 8/648;
 8/918; 8/924; 8/927; 252/301.28; 260/245.6;
 260/925; 427/158; 542/459; 544/140; 544/371;
 546/99, 548/256; 548/327; 548/379
[58] Field of Search ............... 548/217, 256, 327, 379;
 8/648; 252/301.27, 301.28; 260/245.6, 925;
 544/140, 371; 427/158; 542/459; 546/99

[56] References Cited

U.S. PATENT DOCUMENTS

| | | | |
|---|---|---|---|
| 3,507,937 | 4/1970 | Zimmerer | 260/924 |
| 3,630,895 | 12/1971 | Krause | 252/875 |
| 4,001,138 | 1/1977 | Lohmann | 252/301.27 |
| 4,085,101 | 4/1978 | Mercer | 548/379 |
| 4,263,431 | 4/1981 | Weber et al. | 542/459 |
| 4,304,569 | 12/1981 | Engelhardt | 252/301.23 |

FOREIGN PATENT DOCUMENTS 2807497 8/1979 Fed. Rep. of Germany .

Primary Examiner—Arthur P. Demers
Attorney, Agent, or Firm—Edward M. Roberts

[57] ABSTRACT

Cationic fluorescent whitening agents of the formula

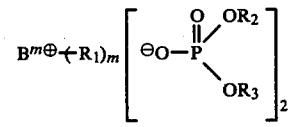

wherein B is a fluorescent whitening agent containing basic tertiary amino groups, m is the number of basic amino groups, and each of $R_1$, $R_2$ and $R_3$ is alkyl of 1 to 4 carbon atoms which is unsubstituted or substituted by non-chromophoric groups, or is alkenyl of 2 to 4 carbon atoms which is unsubstituted or substituted by non-chromophoric groups. These compounds have good solubility in water and they make it possible to prepare concentrated solutions and can be used for whitening organic material.

7 Claims, No Drawings

CATIONIC FLUORESCENT WHITENING AGENTS

This is a division of application Ser. No. 200,738 filed on Oct. 27, 1980, now U.S. Pat. No. 4,384,121.

The present invention relates to novel cationic fluorescent whitening agents, to a process for their production, and to the use thereof for whitening organic material and for the preparation of concentrated aqueous solutions.

A large number of cationic fluorescent whitening agents which are of only limited solubility in water at room temperature are known from the literature. These fluorescent whitening agents are quaternised ammonium salts of basic fluorescent whitening agents which are described e.g. in patent specifications that usually also encompass the basic compounds themselves. Such compounds correspond to those fluorescent whitening agents categorised hereinafter as B.

The invention relates to novel cationic fluorescent whitening agents of the formula

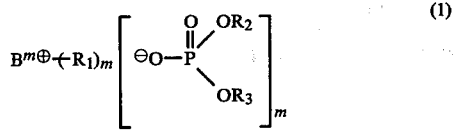

wherein B is a fluorescent whitening agent containing basic tertiary amino groups, m is the number of basic amino groups and each of $R_1$, $R_2$ and $R_3$ is alkyl or alkenyl, each of which contains 1 to 4 carbon atoms and is unsubstituted or substituted by non-chromophoric groups. Suitable fluorescent whitening agents B are, e.g. non-quaternised representatives $B_1$ belonging to the class of 2-furanylbenzimidazoles (cf. U.S. Pat. Nos. 3,497,525; 3,631,168; 3,637,734; 3,900,419; 4,009,994; 4,018,789 and 4,146,725; German Offenlegungsschrift Nos. 2 346 316; 2 807 008; 2 852 531 and 2 821 116; 2-azolylbenzimidazoles (cf. U.S. Pat. No. 4,083,958), 2-stilbenzylbenzimidazoles (cf. U.S. Pat. No. 3,133,916), basic 1,2-bis-(azolyl)ethylenes (cf. U.S. Pat. Nos. 2,808,407; 3,259,619; 3,169,960), 2,5-bis-(benzimidazolyl)-furanes (cf. U.S. Pat. No. 3,005,779), basic 4,4'-bis-(azolyl)stilbenes (cf. U.S. Pat. No. 3,583,984), basic 2-phenyl-5-azolylthiophenes (cf. U.S. Pat. No. 3,264,315), basic 1,3-diphenylpyrazolines (cf. U.S. Pat. Nos. 3,131,079; 3,378,389; 3,574,195; 4,183,853; 3,560,485; 3,690,947; 3,865,816; 3,957,815; 4,045,169; 3,849,406; 4,085,101; 3,598,510; 3,141,879; 4,151,163, 3,753,978; 4,129,563; German Offenlegungsschrift Nos. 2 755 023; 2 346 316; 2 807 008; French patent specification No. 1 431 233), basic 4,4'-distyryl-biphenyls (cf. U.S. Pat. No. 3,984,399), basic 1,4-distyrylbenzenes (cf. U.S. Pat. No. 3,755,446), basic 3,7-disubstituted coumarins (cf. U.S. Pat. Nos. 3,251,851; 3,271,412; 3,625,952; 3,663,560; 4,005,098; German Offenlegungsschrift No. 1 919 181), basic naphthalimides (cf. British patent specification Nos. 962,019 and 1,227,239; U.S. Pat. Nos. 3,697,525; 3,625,947; 3,880,859; 3,941,791; 3,776,932; 4,075,211; German Offenlegungsschrift Nos. 2 064 159; 2 507 459; 2 641 001), basic 4,4'-bis-triazinylaminostilbenes (cf. German Offenlegungsschrift Nos. 1 930 309 and 2 060 085), basic 2-stilben-4-yl-naphthotriazoles (cf. German Auslegeschrift No. 1 090 169) and basic 4,4'-bis-(triazolyl)- and -(pyrazolyl)-stilbenes (cf. U.S. Pat. Nos. 3,824,236 and 3,796,706).

Compared with the compounds of the prior art cited above, the novel cationic fluorescent whitening agents of this invention are distinguished by substantially improved solubility in water and in polar organic solvents at room and elevated temperature. This improved solubility makes it possible to prepare fluorescent whitener solutions with concentrations of up to 60% by weight, preferably of 10 to 50% by weight, of fluorescent whitening agent.

The number of basic amino groups is preferably 1 or 2. However, further basic amino groups can also be present. By basic tertiary amino groups are meant preferably amino groups of aliphatic or aromatic character.

Important cationic fluorescent whitening agents are those of the formula

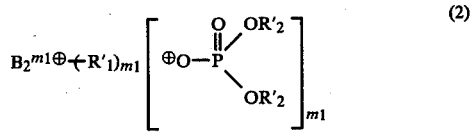

wherein $m_1$ is 1 or 2 and each of $R_1'$ and $R_2'$ is alkyl of 1 to 4 carbon atoms or benzyl and $B_2$ is a fluorescent whitening agent of the formula

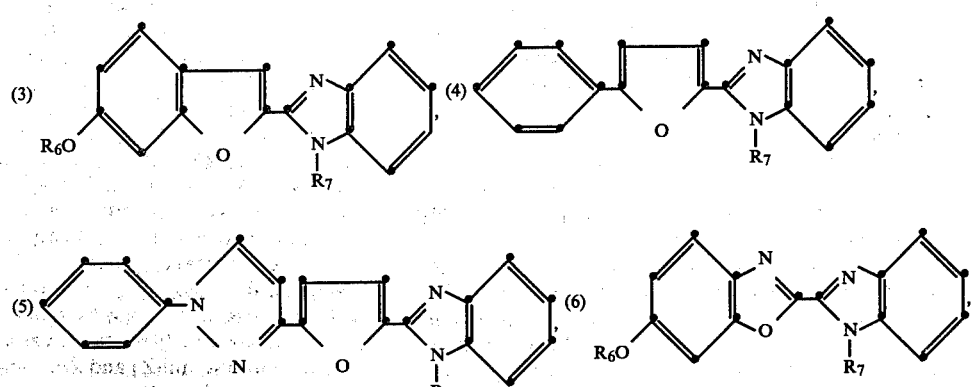

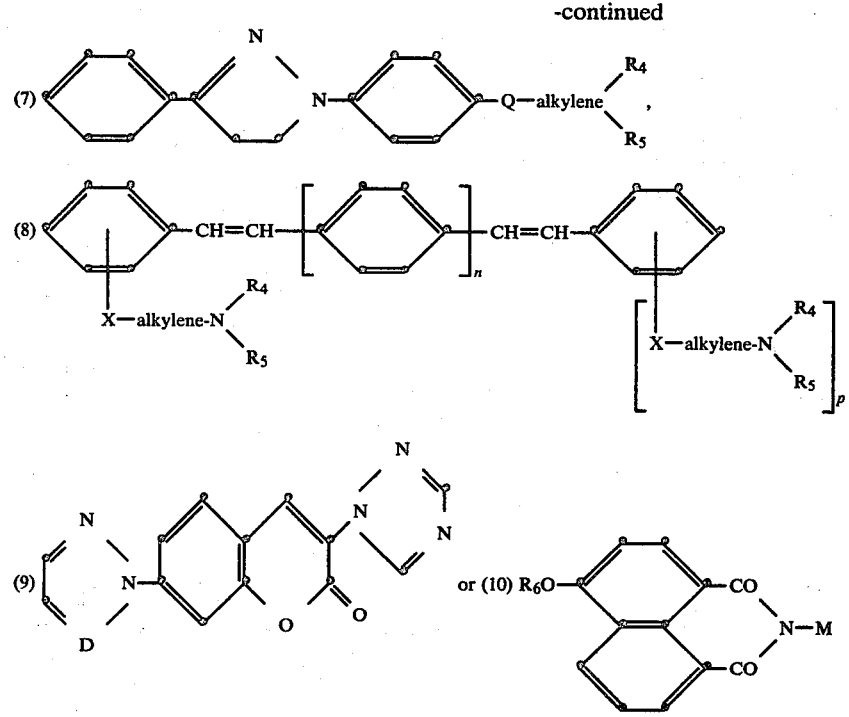

-continued wherein M is alkylene—N(R$_4$)(R$_5$), pyrazolyl or pyridinyl, each of R$_4$ and R$_5$ independently is alkyl of 1 to 6 carbon atoms which is unsubstituted or substituted by non-chromophoric groups, alkenyl of 2 to 6 carbon atoms which is unsubstituted or substituted by non-chromophoric groups, or R$_4$ and R$_5$, together with the nitrogen atom to which they are attached, also form a 5- to 7-membered heterocyclic ring, each of R$_6$ and R$_7$ independently is alkyl of 1 to 6 carbon atoms which is unsubstituted or substituted by non-chromophoric groups, alkenyl of 2 to 6 carbon atoms which is unsubstituted or substituted by non-chromophoric groups, or is phenyl, D is nitrogen or the —CH-group, Q is a non-chromophoric bridge member, X is a non-chromophoric bridge member or the direct bond, n is 1 or 2, and p is 0 or 1, whilst the benzene rings and the heterocyclic rings can also carry non-chromophoric substituents.

Suitable non-chromophoric bridge members Q are groups such as —SO$_2$-alkyleneoxy containing 2 to 8, preferably 2 to 4, carbon atoms in the alkylene moiety, —COO—, —SO$_2$—, —SO$_2$-alkylene-COO—, —SO$_2$-alkylene-CON(R)— and —SO$_2$N(R)—, wherein R is hydrogen or alkyl of 1 to 6, preferably 1 to 4, carbon atoms, which can be substituted e.g. by cyano, carbamoyl, carboxyl, carbalkoxy, hydroxyl, halogen, alkoxy of 1 to 4 carbon atoms, or together with R$_4$ forms a piperazine ring.

Non-chromophoric bridge members X can be oxygen, sulfur, —SO$_2$N(R)—, —CON(R)—, —OCO—, —COO—, the direct bond, —O—C$_{1-3}$alkylene-CON(-R)— or —O—C$_{1-3}$alkylene-COO—.

The "alkylene" radicals can be variously straight-chain or branched and contain 1 to 12, especially 1 to 6, carbon atoms. They can also carry a hydroxyl group.

Suitable alkyl radicals R$_4$ and R$_5$ are those containing 1 to 6, preferably 1 to 4, carbon atoms. They can be substituted e.g. by halogen, cyano, hydroxyl, alkoxy, phenyl or alkoxycarbonyl of 2 to 5 carbon atoms. The radicals R$_4$ and R$_5$ together can form a 5- to 7-membered heterocyclic ring, e.g. a piperidine, pyrrolidine, hexamethyleneimine or morpholine ring, which can be substituted by alkyl groups of 1 to 4 carbon atoms. R$_4$ together with R can also form a piperazine ring.

Alkyl groups R$_6$ which carry non-chromophoric substituents are in particular the alkoxyalkyl group containing a total of 3 to 6 carbon atoms and the benzyl group, whilst R$_7$ is alkyl which is substituted by hydroxyl, alkoxy of 1 to 4 carbon atoms, carbalkoxy of 2 to 5 carbon atoms, cyano, phenyl or carbamoyl.

Alkenyl groups R$_6$ and R$_7$ are preferably unsubstituted and contain preferably 3 to 4 carbon atoms, and the phenyl radicals can be additionally substituted e.g. by 1 to 2 alkyl groups each containing 1 to 4 carbon atoms, chlorine, or alkoxy of 1 to 4 carbon atoms.

Representative examples of non-chromophoric substituents of the benzene or heterocyclic nuclei are: halogen atoms, alkyl groups of 1 to 6 carbon atoms, cyclohexyl groups, alkenyl groups of 3 to 6 carbon atoms, alkoxy groups of 1 to 6 carbon atoms, alkenyloxy groups of 3 to 6 carbon atoms, phenoxy which can additionally be substituted by methyl, chlorine or methoxy; alkylsulfonyl groups of 1 to 6 carbon atoms, phenylsulfonyl or phenoxysulfonyl which can additionally be substituted by methyl, chlorine or methoxy; benzylsulfonyl, cyano, trifluoromethyl, alkoxycarbonyl of 2 to 7 carbon atoms, carboxyl, phenyl, benzyl, —CONZ$_1$Z$_2$ or —SO$_2$NZ$_1$Z$_2$, wherein Z$_1$ is hydrogen, alkyl of 1 to 4 carbon atoms, alkenyl of 3 or 4 carbon atoms, hydroxyalkyl of 2 to 4 carbon atoms, cyclohexyl, alkoxyalkyl containing a total of 3 to 6 carbon atoms, benzyl, or dialkylaminoalkyl containing a total of 3 to 7 carbon atoms which can be quaternised by R$_1$', Z$_2$ is hydrogen, alkyl of 1 to 4 carbon atoms or alkenyl of 3 or 4 carbon atoms, and Z$_1$ and Z$_2$, together with the nitrogen atom to which they are attached, form a pyrrolidine, piperidine, N-alkylpiperazine ring containing 1 to 3 carbon atoms in the alkyl moiety, or a hexamethyleneimine or morpholine ring.

In formula (2), $R_1'$ and $R_2'$ are preferably alkyl of 1 to 3 carbon atoms, $R_4$, $R_5$ and $R_6$ are preferably unsubstituted alkyl radicals of 1 to 4 carbon atoms, whilst $R_4$ and $R_5$ together can form a pyrrolidine, piperidine, hexamethyleneimine or morpholine radical. $R_4$ can also together with R form a piperazine ring. $R_7$ is preferably alkyl of 1 to 4 carbon atoms, alkenyl of 3 or 4 carbon atoms, cyanoalkyl of 2 or 3 carbon atoms, carbalkoxyalkyl containing 1 to 3 carbon atoms in the alkoxy moiety, benzyl or phenyl. D is preferably =N—, X is oxygen, the direct bond, —SO$_2$N(R')—, —CON(R')— or —COO—, and R' is hydrogen, alkyl of 1 to 4 carbon atoms which is unsubstituted or substituted by a cyano group, or together with $R_4$ forms a piperazine ring. The benzene and the heterocyclic rings are preferably substituted by hydrogen, chlorine, alkyl of 1 to 4 carbon atoms or alkoxy of 1 to 4 carbon atoms, and the benzimidazole ring can additionally be substituted by alkylsulfonyl of 1 to 4 carbon atoms, phenylsulfonyl, cyano, trifluoromethyl, phenoxysulfonyl, alkoxycarbonyl containing a total of 2 to 5 carbon atoms, carboxyl, —CONZ$_1'$Z$_2'$ or —SO$_2$NZ$_1'$Z$_2'$, wherein $Z_1'$ is hydrogen, alkyl of 1 to 4 carbon atoms, alkenyl of 3 or 4 carbon atoms, hydroxyalkyl of 2 to 4 carbon atoms, alkoxyalkyl containing a total of 3 to 6 carbon atoms, cyclohexyl or benzyl, and $Z_2'$ is hydrogen, alkyl of 1 to 4 carbon atoms, or $Z_1'$ and $Z_2'$, together with the nitrogen atom, can also form a morpholine ring.

Especially important cationic fluorescent whitening agents are those of the formula

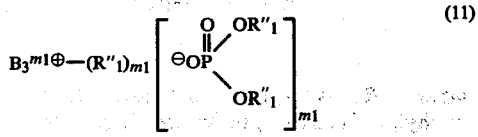

(11)

wherein $m_1$ is 1 or 2 and $R_1''$ is alkyl of 1 to 3 carbon atoms and $B_3$ is a fluorescent whitener radical of the formula

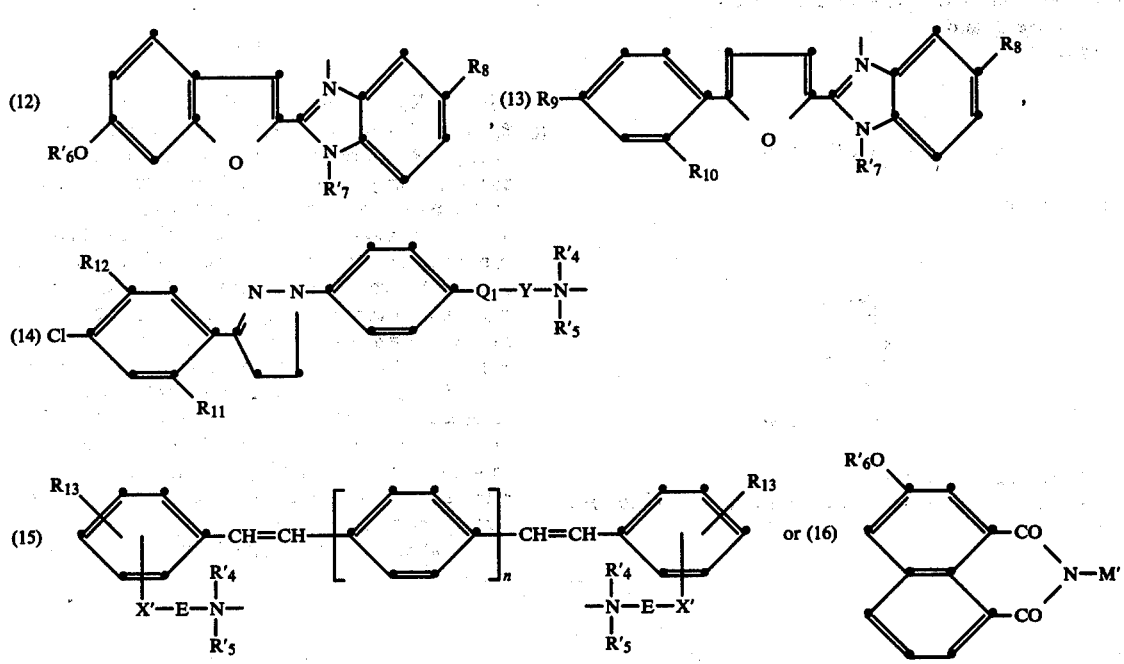

in which radicals $R_6'$ is alkyl or 1 to 4 carbon atoms, $R_7'$ is alkyl of 1 to 4 carbon atoms, benzyl, phenyl, alkenyl of 3 to 4 carbon atoms, cyanoalkyl of 2 or 3 carbon atoms, alkoxycarbonylmethyl containing 1 to 3 carbon atoms in the alkoxy moiety, $R_8$ is hydrogen, methyl, chlorine, alkylsulfonyl of 1 to 4 carbon atoms, phenylsulfonyl, cyano, trifluoromethyl, phenoxysulfonyl, alkoxycarbonyl containing a total of 2 to 5 carbon atoms, carboxyl, —CONZ$_1'$Z$_2'$ or —SO$_2$NZ$_1'$Z$_2'$, wherein $Z_1'$ is hydrogen, alkyl or 1 to 4 carbon atoms, alkenyl of 3 or 4 carbon atoms, hydroxyalkyl of 2 to 4 carbon atoms, alkoxyalkyl containing a total of 3 to 6 carbon atoms, or benzyl, and $Z_2'$ is hydrogen, alkyl of 1 to 4 carbon atoms, or $Z_1'$ and $Z_2'$, together with the nitrogen atom to which they are attached, can also form a morpholine ring, $R_9$, $R_{10}$, $R_{11}$ and $R_{12}$, each independently of the other, are hydrogen, chlorine or methyl, $Q_1$ is —COO— or, preferably, —SO$_2$—, Y is alkylene of 2 to 4 carbon atoms, —N(R')-alkylene containing 2 to 4 carbon atoms in the alkylene moiety, alkyleneoxyalkylene containing a total of 4 to 7 carbon atoms, alkylene-COO-alkylene or alkylene-CONH-alkylene, each containing a total of 4 to 7 carbon atoms, R' is hydrogen, alkyl of 1 to 4 carbon atoms which is unsubstituted or substituted by a cyano group, or together with $R_4'$ is a piperazine radical, X' is oxygen, sulfur, the direct bond, —SO$_2$NR'—, —CONR' or —COO—, E is alkylene of 1 to 4 carbon atoms which is unsubstituted or substituted by a —OH group, $R_4'$ is alkyl of 1 to 4 carbon atoms, or together with R' is a piperazine radical or together with $R_5'$ is a pyrrolidine, piperidine, hexamethyleneimine or morpholine radical, $R_5'$ is alkyl of 1 to 4 carbon atoms, or together with $R_4'$ is a pyrrolidine, piperidine, hexamethyleneimine or morpholine radical, $R_{13}$ is hydrogen, chlorine, alkyl of 1 to 4 carbon atoms or alkoxy of 1 to 4 carbon atoms, n is 1 or 2, and M is -alkylene-N(R'$_4$R'$_5$)

or the radical

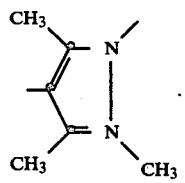

Of particular interest are (a) cationic fluorescent whitening agents of the formula (17)

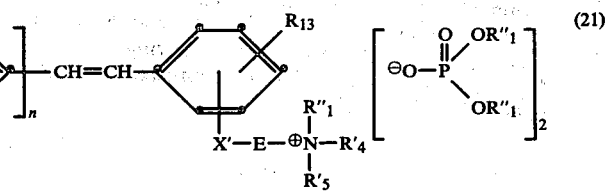

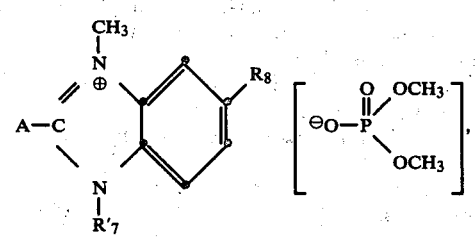

wherein A is a radical of the formula

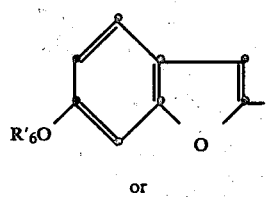

or

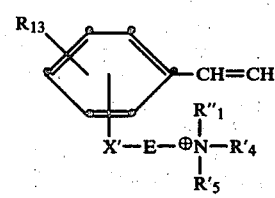

(18)

-continued wherein $R_6'$ is alkyl of 1 to 4 carbon atoms and each of $R_9$ and $R_{10}$ independently is hydrogen, chlorine or methyl, $R_7'$ is alkyl of 1 to 4 carbon atoms, benzyl, phenyl, alkenyl of 3 or 4 carbon atoms, cyanoalkyl of 2 or 3 carbon atoms, alkoxycarbonylmethyl containing 1 to 3 carbon atoms in the alkoxy moiety, and $R_8$ is hydrogen, methyl, chlorine, alkylsulfonyl of 1 to 4 carbon atoms, phenylsulfonyl, cyano, trifluoromethyl, phenoxysulfonyl, alkoxycarbonyl containing a total of 2 to 5 carbon atoms, carboxyl, $CONZ_1'Z_2'$ or $SO_2NZ_1'Z_2'$, wherein $Z_1'$ is hydrogen, alkyl of 1 to 4 carbon atoms, alkenyl of 3 or 4 carbon atoms, hydroxyalkyl of 2 to 4 carbon atoms, alkoxyalkyl containing a total of 3 to 6 carbon atoms, or benzyl, and $Z_2'$ is hydrogen, alkyl of 1 to 4 carbon atoms, or $Z_1'$ and $Z_2'$, together with the nitrogen atom to which they are attached, can also form a morpholine ring, (b) cationic fluorescent whitening agents of the formula (20)

wherein $R_1''$ is alkyl of 1 to 3 carbon atoms, preferably methyl, $R_4'$ is alkyl of 1 to 4 carbon atoms, or together with $R'$ is a piperazine radical or together with $R_5'$ is a pyrrolidine, piperidine, hexamethyleneimine or morpholine radical, $R_5'$ is alkyl of 1 to 4 carbon atoms, or together with $R_4'$ is a pyrrolidine, piperidine, hexamethyleneimine or morpholine radical, $R_{11}$ and $R_{12}$ are hydrogen, methyl or chlorine, Y is alkylene of 2 to 4 carbon atoms, —N(R')-alkylene containing 2 to 4 carbon atoms in the alkylene moiety, alkyleneoxyalkylene containing a total of 4 to 7 carbon atoms, alkylene-COO-alkylene containing a total of 4 to 7 carbon atoms or alkylene-CONH-alkylene containing a total of 4 to 7 carbon atoms, and $R'$ is hydrogen, alkyl of 1 to 4 carbon atoms which is unsubstituted or substituted by a cyano group, or together with $R_4'$ forms a piperazine ring, as well as (c) cationic fluorescent whitening agents of the formula (21)

wherein $R_1''$ is alkyl of 1 to 3 carbon atoms, preferably methyl, X' is oxygen, sulfur, the direct bond, —COO—, —CON(R")— or —SO$_2$N(R")—, and X' is preferably in the 2- or 3-position, R" is hydrogen, alkyl of 1 to 4 carbon atoms, or together with R4' is a piperazine radical, E is alkylene of 1 to 4 carbon atoms which is unsubstituted or substituted by an —OH group, R4' is alkyl of 1 to 4 carbon atoms, or together with R" is a piperazine radical or together with R5' is a pyrrolidine, piperidine, hexamethyleneimine or morpholine radical, R5' is alkyl alkylene moiety, alkyleneoxyalkylene containing a total of 4 to 7 carbon atoms or alkylene-CON(R''')-alkylene containing a total of 4 to 7 carbon atoms, and R''' is hydrogen, cyanoethyl, or together with R4" forms a piperazine ring, as well as (f) cationic fluorescent whitening agents of the formula

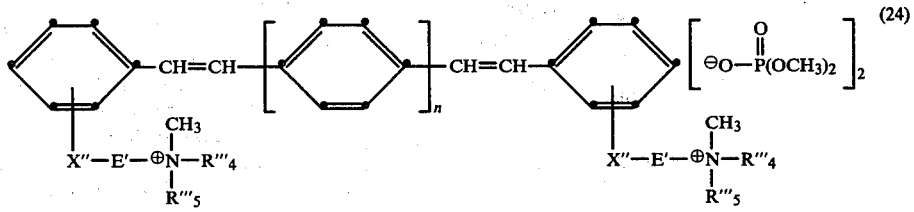

of 1 to 4 carbon atoms or together with R4' is a pyrrolidine, piperidine, hexamethyleneimine or morpholine radical, R13 is hydrogen, chlorine, alkyl of 1 to 4 carbon atoms or alkoxy of 1 to 4 carbon atoms, and n is 1 or 2.

Most preferred are (d) cationic fluorescent whitening agents of the formula

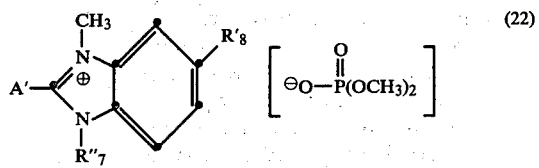

wherein A' is a radical of the formula

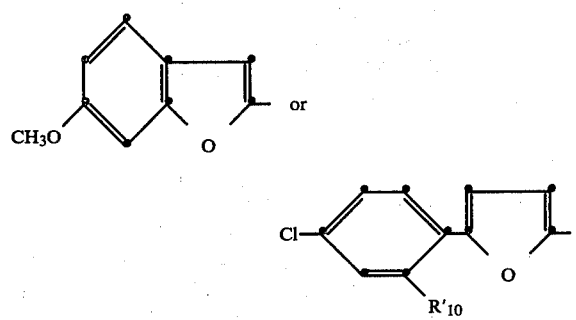

R7" is alkyl of 1 to 4 carbon atoms, benzyl, phenyl, or cyanoalkyl of 2 or 3 carbon atoms, R8' is hydrogen, alkylsulfonyl of 1 to 4 carbon atoms, phenylsulfonyl, phenoxysulfonyl, sulfamoyl, alkylsulfamoyl of 1 to 4 carbon atoms, alkoxycarbonyl of 2 to 4 carbon atoms, cyano or chlorine, and R10' is hydrogen, chlorine or methyl, (e) cationic fluorescent whitening agents of the formula

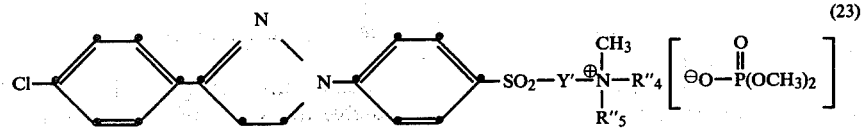

wherein R4" is alkyl of 1 or 2 carbon atoms, or together with R''' forms a piperazine ring, R5" is alkyl of 1 or 2 carbon atoms, Y' is alkylene of 2 to 4 carbon atoms, —N(R''')-alkylene containing 2 to 4 carbon atoms in the wherein X" is oxygen, the direct bond, —SO2NH— or —CONH— in the 2- or 3-position, E' is alkylene of 1 to 3 carbon atoms, R4''' and R5''' are alkyl of 1 or 2 carbon atoms, or together are a pyrrolidine, piperidine or morpholine radical, and n is 1 or 2.

The cationic fluorescent whitening agents of the formula (1) are obtained in a manner known per se by quaternising a fluorescent whitening agent B with at least stoichiometric amounts m of a phosphate of the formula

wherein R1, R2 and R3 have the meanings given above, in the temperature range from 60° to 200° C., and optionally in an inert solvent.

Preferred phosphates of the formula (25) are: trimethylphosphate, triethylphosphate, triisopropylphosphate, tri-n-propylphosphate, dibutylmethylphosphate, tribenzylphosphate, diisopropylmethylphosphate, triallylphosphate, tributylphosphate, tris-(2-chloroethyl)-phosphate and tris-(methoxyethyl)phosphate. Trimethylphosphate is particularly preferred. It is also possible to quaternise bases of cationic dyes with these trialkylphosphates.

Suitable reaction media in which the quaternisation can be carried out are in general all inert solvents. Preferred solvents are those in which the starting material dissolves and from which the final product precipitates immediately. Examples of such solvents are: aromatic hydrocarbons, such as benzene, toluene and xylene; halogenated hydrocarbons, such as trichloroethane, tetrachloroethylene, chlorobenzene or dichlorobenzene, and also nitrobenzene; alkanols and open or cyclic ethers, such as butanol, dibutyl ether, ethylene glycol monomethyl ether, ethylene glycol monoethyl ether, anisole or dioxane; ketones, such as cyclohexanone or methyl ethyl ketone; fatty acid amides, such as dimethyl formamide or dimethyl acetamide; sulfoxides, such as dimethyl sulfoxide; and esters and nitriles of carboxylic acids, such as ethyl acetate, butyl acetate, acetonitrile or methoxypropionitrile. The reaction is carried out for example in the temperature range from 60° to 200° C., preferably from 80° to 170° C. On occasion it is also advantageous to use water as solvent.

A particularly advantageous process comprises carrying out the reaction in an excess of alkylating agent in the temperature range from 60° to 200° C., preferably from 100° to 170° C., whereupon the reaction product often precipitates on cooling or by addition of a suitable solvent, e.g. one of those mentioned above.

As the resultant cationic fluorescent whitening agents are particularly readily soluble in water, a reaction mixture which still contains an excess of water-soluble phosphate of the formula (25) can also be diluted with water without isolation of the fluorescent whitening agent, in order thus to obtain a ready-for-use concentrated solution. The invention also relates to such concentrated solutions. Purely aqueous solutions are obtained by dissolving the isolated cationic fluorescent whitening agents in the desired amount of water.

To stabilise the aqueous solutions against a possible phosphate hydrolysis, it is possible to add to these solutions a pH buffer substance, e.g. sodium acetate or sodium lactate. A good buffer action is also obtained by neutralising the initially usually acidic aqueous solutions containing excess phosphate with alkali metal hydroxides (e.g. sodium hydroxide), alkali metal carbonates or bicarbonates, water-soluble basic amines, or ammonia.

The starting materials of the formula (25) used for the quaternisation are known or they are obtained by methods analogous to known ones.

The novel compounds defined above exhibit a more or less pronounced fluorescence in the dissolved or finely divided state. They can be used for whitening a wide variety of synthetic, regenerated man-made or natural organic materials or substances which contain such organic materials.

The organic materials to be whitened can be in the most widely different states of processing (raw materials, semi-finished goods or finished goods).

The compounds of the present invention are of importance, inter alia, for the treatment of textile organic materials, especially woven textiles.

Depending on the type of fluorescent whitening agent used, it can be advantageous to carry out the treatment in a neutral, alkaline or acid bath. The treatment is usually carried out in the temperature range from 20° to 140° C., for example at the boiling point of the bath or near it (above 90° C.). Solutions or emulsions in organic solvents can also be used for the treatment of textile substrates according to the invention, as is practised in the dyeing industry in solvent dyeing (pad-thermofixation application, or exhaustion dyeing processes in dyeing machines).

The fluorescent whitening agents of the present invention can, for example, also be employed in the following formulation:

(a) in mixtures with dyes (shading) or pigments (coloured pigments or especially, for example, white pigments), or as an additive in dyebaths, printing pastes, discharge pastes or reserve pastes, or for the aftertreatment of dyeings, prints or discharge prints;

(b) in mixtures with wetting agents, plasticisers, swelling agents, antioxidants, ultraviolet absorbers, heat stabilisers and chemical bleaching agents (chlorite bleach or bleaching bath additives);

(c) in admixture with crosslinking agents or finishing agents (for example starch or synthetic finishes), and in combination with a wide variety of textile finishing processes, especially synthetic resin finishes (for example creaseproof finishes such as wash-and-wear, permanent-press or non-iron), as well as flameproof finishes, fabric softening finishes, antisoiling finishes or antistatic finishes, or antimicrobial finishes;

(d) incorporation of the fluorescent whitening agents into polymer carriers (polymerisation, polycondensation or polyaddition products, in dissolved or dispersed form, for use e.g. in coating agents, impregnating agents or binders (solutions, dispersions and emulsions) for textiles, non-wovens, papers and leather;

(e) as additives in master batches;

(f) as additives in a wide variety of industrial products in order to render these more marketable (for example improving the appearance of soaps, detergents, pigments);

(g) in combination with other optically brightening substances;

(h) in spinning bath preparations, that is to say as additives in spinning baths which are used for improving the slip for the further processing of synthetic fibres, or from a special bath before the streching of the fibre;

(i) as scintillators for various purposes of a photographic nature, for example for electrophotographic reproduction or supersensitising;

If the whitening method is combined with textile treatment of finishing methods, the combined treatment can in many cases advantageously be carried out with the aid of appropriate stable preparations which contain the fluorescent whitening agents in a concentration such that the desired white effect is achieved.

In certain cases, the fluorescent whitening agents are made fully effective by an aftertreatment. This can be, for example, a chemical treatment (for example acid treatment), a heat treatment or a combined chemical/-heat treatment.

The amount of fluorescent whitening agents of the present invention to be used, based on the weight of the material to be whitened, can vary within wide limits. A marked and lasting effect can be obtained even with very insignificant amounts, in certain cases, e.g. 0.0001 percent by weight. But it is also possible to use amounts of up to about 0.8 percent by weight and, on occasion, up to about 2 percent by weight. For most practical purposes, it is preferable to use amounts between 0.005 and 0.5 percent by weight.

For various reasons it is often advantageous not to use the fluorescent whitening agents by themselves, i.e. pure, but in admixture with a wide variety of assistants and extenders, for example anhydrous sodium sulfate, sodium sulfate decahydrate, sodium chloride, sodium carbonate, alkali metal phosphates, such as sodium or potassium orthophosphate, sodium or potassium pyrophosphate and sodium or potassium tripolyphosphates or alkali metal silicates.

The cationic fluorescent whitening agents of the present invention are suitable for whitening organic material, especially polyacrylonitrile, polyamide and cellulose.

In the following Examples, percentages are by weight. Unless otherwise indicated, melting and boiling points are uncorrected.

EXAMPLE 1

With stirring and while introducing a weak flow of nitrogen, 7.1 g of the compound of the formula

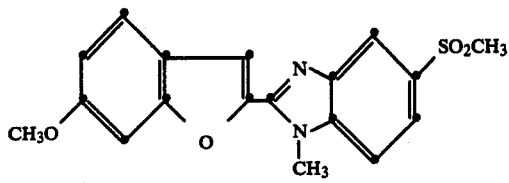
(100)

are heated in 20 ml of trimethylphosphate for 60 minutes to 160° C. After this time, a sample forms a clear solution in water. While cooling, the reaction mixture is diluted with 50 ml of ethyl acetate and the crystallised product is filtered with suction at room temperature. The residue, which deliquesces in air, is washed repeatedly with ethyl acetate and dried immediately in vacuo at 100° C., affording 10.8 g of compound of the formula

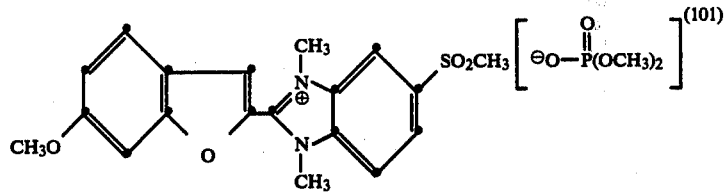
(101)

(m.p. 115° C.) which additionally contains 1 mole of trimethylphosphate crystals and 1 mole of water of crystallisation.

Recrystallisation of this product from 1,2-dichloroethane, or addition of methyl ethyl ketone instead of ethyl acetate to the still hot reaction mixture obtained in the process, yields a product with a melting point of 181° C. which contains no more trimethylphosphate crystals. The solubility of this product at room temperature is more than 100 g in 100 ml of water, and that of the corresponding methosulfate is 0.5 g.

EXAMPLE 2

With stirring and while introducing a weak flow of nitrogen, 7.1 g of the compound of the formula

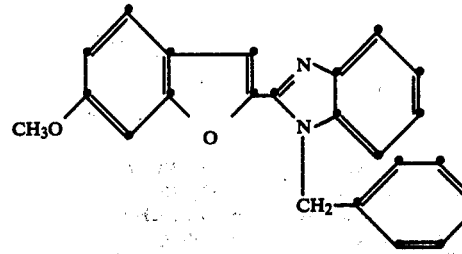
(200)

are heated in 20 ml of trimethylphosphate for 60 minutes to 160° C. After this time, a sample forms a clear solution in water. The reaction mixture is cooled to room temperature to give the compound of the formula

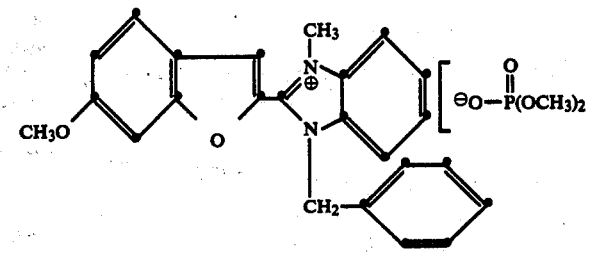
(201)

in excess trimethylphosphate, in the form of a viscous oil which can be diluted to any degree with water without precipitation. A 19% solution was unchanged in aspect after storage for several months. The pH also remainded unchanged on storage after neutralisation of a sample with sodium hydroxide. The solubility of the corresponding methosulfate in water is 0.5%.

The fluorescent whitening agents of the formula

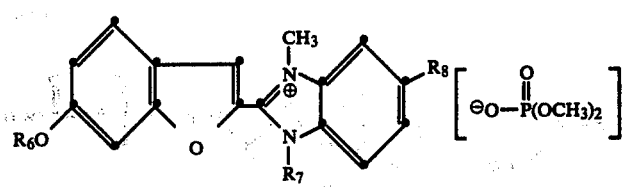
(202)

listed in Table I are obtained in a manner similar to that described in Example 1 or 2:

TABLE I

| formula | R₆ | R₇ | R₈ | UV λ_max in polyacrylonitrile (nm) |
|---|---|---|---|---|
| 203 | CH₃ | CH₃ | —SO₂NHCH₃ | 365 |
| 204 | CH₃ | CH₃ | —SO₂N(CH₃)₂ | 365 |
| 205 | CH₃ | CH₃ | —SO₂NH₂ | 363 |
| 206 | CH₃ | CH₃ | —SO₂N(morpholino) | 366 |
| 207 | CH₃ | C₂H₅ | —SO₂NHC₂H₅ | 362 |
| 208 | CH₃ | CH₂C₆H₅ | —SO₂NH₂ | 367 |
| 209 | CH₃ | CH₂CH=CH₂ | —SO₂NHCH₂CH=CH₂ | 366 |
| 210 | CH₃ | n-C₄H₉ | —SO₂NH₂ | 362 |
| 211 | CH₃ | CH₃ | —SO₂NHCH₂CH₂OCH₃ | 365 |
| 212 | CH₃ | CH₂C₆H₅ | —SO₂NHCH₂C₆H₅ | 367 |
| 213 | CH₃ | C₂H₅ | —SO₂NH₂ | 362 |
| 214 | nC₄H₉ | CH₃ | —SO₂NHCH₃ | 367 |
| 215 | CH₃ | CH₃ | —COOH | 364 |
| 216 | CH₃ | CH₃ | —COOC₂H₅ | 364 |
| 217 | CH₃ | C₂H₅ | —COOH | 362 |
| 218 | CH₃ | CH₃ | —CONHCH₃ | 360 |
| 219 | CH₃ | CH₃ | —COOCH₃ | 364 |
| 220 | CH₃ | CH₂C₆H₅ | —CONH₂ | 365 |
| 221 | CH₃ | CH₃ | —CN | 370 |
| 222 | CH₃ | CH₃ | —SO₂OC₆H₅ | 370 |
| 223 | CH₃ | CH₃ | —SO₂C₆H₅ | 369 |
| 224 | CH₃ | CH₃ | —CF₃ | 360 |
| 225 | CH₃ | CH₂C₆H₅ | —CF₃ | 364 |
| 226 | CH₃ | CH₂CH₂CN | H | 361 |
| 227 | CH₃ | CH₂C₆H₅ | —Cl | 363 |
| 228 | CH₃ | CH₃ | SO₂NHCH₂CH₂OH | 363 |
| 229 | CH₃ | CH₂COOCH₃ | H | 357 (in DMF) |
| 230 | CH₃ | CH₂CN | H | 360 |
| 231 | CH₃ | CH₂C₆H₅ | CH₃ | 357 |

EXAMPLE 3

With stirring and while introducing a weak flow of nitrogen, 7 g of the compound of the formula

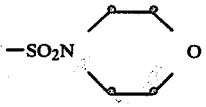

are heated in 30 ml of trimethylphosphate for 2 hours to 160° C. While cooling, the densely precipitated product is diluted with 30 ml of methyl ethyl ketone and filtered with suction at room temperature. The residue is washed repeatedly with methyl ethyl ketone and dried in vacuo at 100° C., affording 7 g of a pale yellow crystalline product of the formula with a melting point of 246° C. The solubility of this product in water at 80° C. is 10%, and that of the corresponding methosulfate is 0.3%.

The compounds of the formula

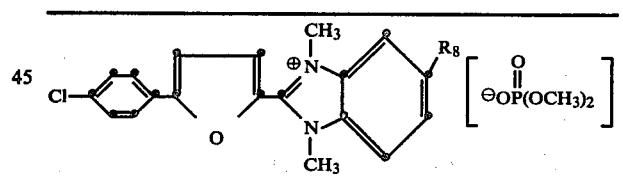

| No. | R₈ | m.p. | Solubility in H₂O at room temperature |
|---|---|---|---|
| (302) | —SO₂CH₃ | 270° C. | 17% |
| (303) | —CN | 220° C. | 3.4% | are obtained in analogous manner.

The solubility of each of the corresponding methosulfates in water at room temperature is about 0.1%.

The fluorescent whitening agents of the formula

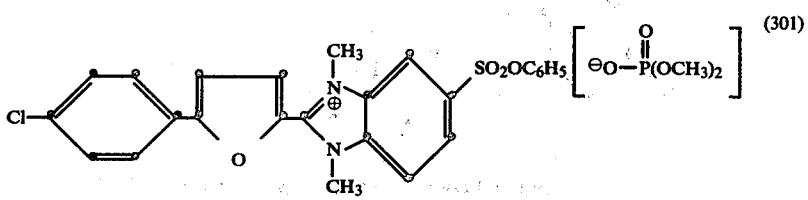

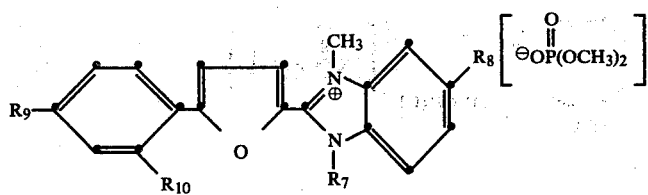

listed in Table II can also be obtained in the above described manner.

lised product is collected by filtration. The residue is washed repeatedly with methyl ethyl ketone and dried

TABLE II

| formula | $R_7$ | $R_{10}$ | $R_9$ | $R_8$ | UV$\lambda_{max}$ in polyacrylonitrile (nm) |
|---|---|---|---|---|---|
| 304 | $C_6H_5$ | Cl | Cl | H | 357 |
| 305 | $CH_3$ | H | $CH_3$ | $SO_2OC_6H_5$ | 357 |
| 306 | $CH_3$ | H | $COOC_2H_5$ | $SO_2CH_3$ | 363 |
| 307 | $CH_3$ | $CH_3$ | Cl | $SO_2CH_3$ | 360 |
| 308 | $CH_3$ | H | Cl | $SO_2C_6H_5$ | 366 |
| 309 | $CH_2C_6H_5$ | H | Cl | $SO_2CH_3$ | 364 |
| 310 | $CH_2CH_2CN$* | H | Cl | $SO_2CH_3$ | 367 |
| 311 | $CH_3$ | H | Cl | $SO_2C_2H_5$ | 364 |
| 312 | $C_2H_5$ | H | Cl | $SO_2CH_3$ | 361 |
| 313 | $CH_3$ | H | H | $SO_2CH_3$ | 362 |
| 314 | $CH_2CN$* | H | Cl | $SO_2CH_3$ | 372 |
| 315 | $CH_2C_6H_5$ | H | Cl | $SO_2N(CH_3)_2$ | 364 |
| 316 | $C_4H_9$ | H | Cl | $SO_2NH_2$ | 361 |
| 317 | $CH_2C_6H_5$ | H | Cl | $SO_2NHCH_2C_6H_5$ | 365 |
| 318 | $CH_2CH=CH_2$ | H | Cl | $SO_2NHCH_2CH=CH_2$ | 362 |
| 319 | $CH_3$ | H | Cl | $CONHCH_3$ | 362 |
| 320 | $CH_3$ | H | Cl | $COOCH_3$ | 363 |
| 321 | $CH_3$ | H | Cl | $COOH$ | 363 |
| 322 | $CH_2C_6H_5$ | H | Cl | $CONH_2$ | 363 |

*mixture of isomers ($R_7$ and $CH_3$ exchanged).

EXAMPLE 4

With stirring, 6.7 g of the compound of the formula

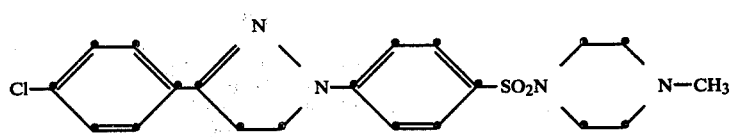

are heated in 8.4 g of trimethylphosphate for 15 minutes to 110°–120° C. After this time, a sample forms a clear solution in water. The reaction mixture is diluted with 50 ml of methyl ethyl ketone, cooled, and the crystalin vacuo at 100° C., affording 8.8 g of compound of the formula

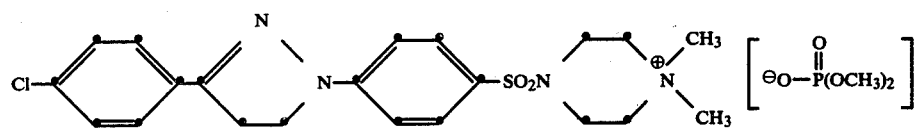

(m.p. 143° C.) which contains about 2 moles of water of (400)

crystallisation. The solubility of this product in water at room temperature is over 50%, and that of the corresponding methosulfate is 0.08%.

The compounds of the formulae (402) and (403)

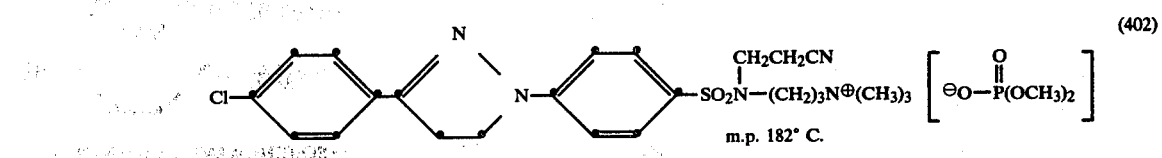

(402)

m.p. 182° C.

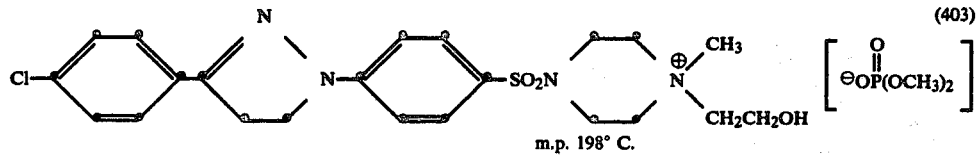

m.p. 198° C.

are obtained in analogous manner.

The solubility of the compound of the formula (402) at room temperature is over 100 g in 100 ml of water, and that of the corresponding methosulfate or chloride is about 1 g. The solubility of the compound of the formula (403) in water at room temperature is about 42%, and that of the corresponding methosulfate is 0.05%.

The fluorescent whitening agents of the formula

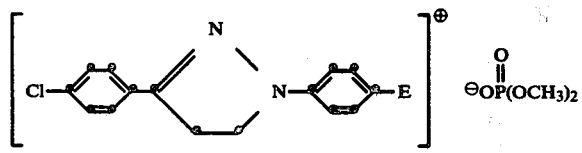

listed in Table III

TABLE III

| formula | E | m.p. | Solubility in H₂O at room temperature |
|---|---|---|---|
| (405) | —SO₂NH(CH₂)₃—N(CH₃)₃ | 181° C. | 46% |
| (406) | —SO₂(CH₂)₂OCHCH₂—N(CH₃)₃<br>                                        \|<br>                                       CH₃ | 177° C. | above 67% |
| (407) | —SO₂(CH₂)₂CONH(CH₂)₃—N(CH₃)₃ | 183° C. | above 50% | and those of the formula

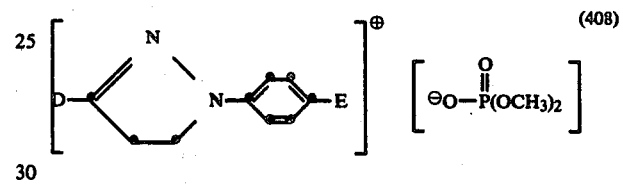

listed in Table IIIa, are also obtained in analogous manner.

TABLE IIIa

| Formula | D | E |
|---|---|---|
| 409 | 4-chlorophenyl- | —SO₂(CH₂)₃—N(CH₃)₃ |
| 410 | " | —SO₂CH₂CH—N(CH₃)₃<br>        \|<br>        CH₃ |
| 411 | 4,5-dichloro-2-methylphenyl | —SO₂NH(CH₂)₃—N(CH₃)₃ |
| 412 | 4,5-dichlorophenyl- | —SO₂(CH₂)₃—N(CH₃)₃ |
| 413 | 4,5-dichloro-2-methylphenyl | —SO₂(CH₂)₂—N(CH₃)₃ |
| 414 | 4-chlorophenyl | —SO₂(CH₂)₂O(CH₂)₂—N(CH₃)₃ |
| 415 | " | —SO₂(CH₂)₂O(CH₂)₂—N⟨CH₃, morpholine ring⟩ |
| 416 | " | —SO₂(CH₂)₂O(CH₂)₂—N(CH₃)(C₂H₅)₂ |
| 417 | " | —SO₂(CH₂)₂O(CH₂)₂—N(CH₃)(C₄H₉)₂ |
| 418 | 4,5-dichloro-2-methylphenyl | SO₂(CH₂)₂OCHCH₂—N(CH₃)₃<br>             \|<br>             CH₃ |
| 419 | " | —SO₂(CH₂)₂O(CH₂)₂—N(CH₃)₃ |
| 420 | " | —SO₂NH(CH₂)₂—N(CH₃)(C₂H₅)₂ |
| 421 | " | —COO(CH₂)₂—N(CH₃)₃ |
| 422 | 4-chlorophenyl | —COO(CH₂)₂—N(CH₃)₃ |
| 423 | " | —SO₂CH₂CHO(CH₂)₂—N⟨ring, CH₃⟩<br>         \|<br>         CH₃ |
| 424 | " | —SO₂(CH₂)₂CONH(CH₂)₂—N(CH₃)₃ |
| 425 | " | —SO₂(CH₂)₂CON⟨piperazine⟩N(CH₃)₂ |
| 426 | " | —SO₂(CH₂)₂COO(CH₂)₂—N(CH₃)₃ |

TABLE IIIa-continued

| Formula | D | E |
|---|---|---|
| 427 | " | —SO₂(Ch₂)₂COOCH(CH₃)—CH₂—N(CH₃)₃ |
| 428 | " | —SO₂(CH₂)₂COO(CH₂)₃—N(CH₃)₃ |
| 429 | " | —SO₂CH₂CHO(CH₃)(CH₂)₂—N(CH₃)(C₂H₅)₂ |
| 430 | " | —SO₂CH₂CHO(CH₃)(CH₂)₃—N(CH₃)₃ |
| 431 | " | —SO₂CH₂CHO(CH₃)(CH₂)₂—N(CH₃)(morpholino) |
| 432 | " | —SO₂CH₂CHO(CH₃)(CH₂)₂—N(CH₃)₃ |
| 433 | " | —SO₂CH₂CH(CH₃)OCH₂CH(CH₃)N(CH₃)₃ |
| 434 | " | —SO₂CH₂CHO(CH₃)(CH₂)₃N(CH₃)(piperidino) |
| 435 | 4,5-dichloro-2-methylphenyl | —SO₂CH₂—CHO(CH₃)(CH₂)₂N(CH₃)₃ |

EXAMPLE 5

With stirring, 5.6 g of the compound of the formula

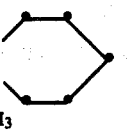
(500)

are heated in 30 ml of trimethylphosphate for 60 minutes to 100° C., whereupon the reaction product crystallises out. After this time, a sample forms a clear solution in water. The reaction mixture is diluted with 30 ml of methyl ethyl ketone, cooled, and the residue is filtered with suction and washed repeatedly with methyl ethyl ketone, then dried in vacuo at 100° C., affording 7.2 g of compound of the formula

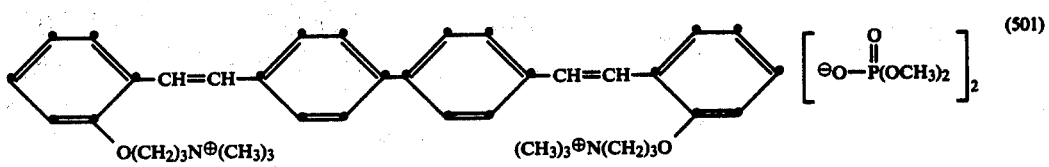
(501)

in almost colourless crystals with a melting point of 270° C. (with decompos.).

This product dissolves in water at room temperature to give a clear solution in a concentration of about 40%, compared with 11% for the corresponding methosulfate.

The compound of the formula

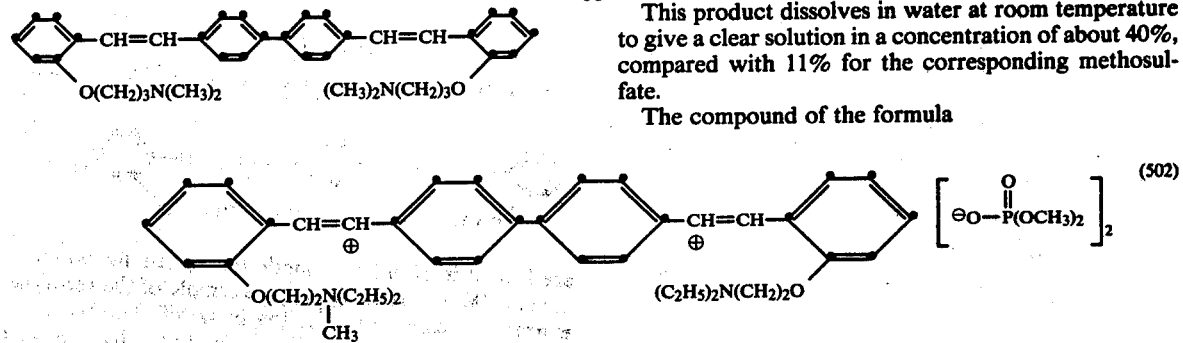
(502)

(m.p. 190° C.), which contains about 3½ moles of water of crystallisation, is obtained in analogous manner. The solubility of this product in water is at least 50%, and that of the corresponding methosulfate is 16%.

Heating the compound of the formula (500) with triethylphosphate at 150° C. instead of with trimethylphosphate and repeating the same procedure yields 6.5 g of the compound of the formula

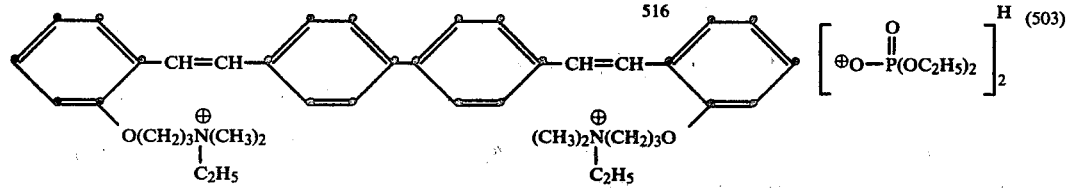

(503)

which can be recrystallised from 1,2-dichloroethane and contains 1½ moles of water of crystallisation (m.p. about 153° C.). The solubility of this product in water is about 40%.

The fluorescent whitening agents of the formula

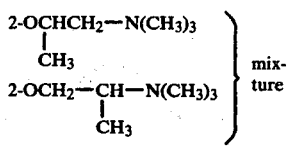
mixture

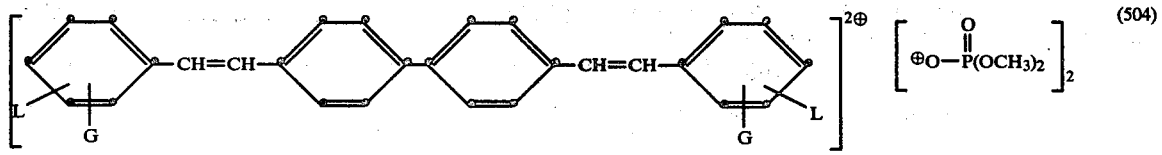
(504)

listed in Table IV are obtained in a manner similar to that described in the foregoing Examples.

TABLE IV

| Formula | G | L | $\lambda_{max}$ in dimethyl formamide (nm) |
|---|---|---|---|
| 505 | 2-O(CH$_2$)$_2$—N(CH$_3$)$_3$ | H | 362 |
| 506 | 2-SO$_2$NH(CH$_2$)$_3$—N(CH$_3$)$_3$ | H | 355 |
| 507 | 2-SO$_2$NH(CH$_2$)$_2$—N(CH$_3$)$_3$ | H | 357 |
| 508 | 2-SO$_2$NH(CH$_2$)$_3$—NCH$_3$(C$_2$H$_5$)$_2$ | H | 351 |
| 509 | 2-SO$_2$N(morpholine-like ring with CH$_3$, CH$_3$) | H | 357 |
| 510 | 3-SO$_2$NH(CH$_2$)$_3$—N(CH$_3$)$_3$ | 4-Cl | 362 |
| 511 | 2-CONH(CH$_2$)$_3$—N(CH$_3$)$_3$ | H | 351 |
| 512 | 2-O(CH$_2$)$_2$—N(CH$_3$, morpholine) | H | 361 |
| 513 | 2-O(CH$_2$)$_2$—N(CH$_3$, piperidine) | H | 360 |
| 514 | 2-O(CH$_2$)$_2$—N(CH$_3$, pyrrolidine) | H | 361 |
| 515 | | | H |
| 516 | | | H |
| 517 | 3-O(CH$_2$)$_2$—N(C$_2$H$_5$)$_2$ with CH$_3$ | H | 356 |
| 518 | 2-OCH$_2$CHCH$_2$—N(CH$_3$)$_3$ with OH | H | 362 |
| 519 | 2-S(CH$_2$)$_2$—N(CH$_3$)$_3$ | H | 358 |
| 520 | 2-O(CH$_2$)$_3$—N(CH$_3$)$_3$ | 3-OCH$_3$ | 356 |
| 521 | 2-O(CH$_2$)$_3$—N(CH$_3$)$_3$ | 5-Cl | 367 |
| 522 | 2-O(CH$_2$)$_3$—N(CH$_3$)$_3$ | 5-CH$_3$ | 366 |
| 523 | 2-CH$_2$N(CH$_3$)$_3$ | H | 352 |
| 524 | 4-O—(CH$_2$)$_2$—N(C$_2$H$_5$)$_2$ with CH$_3$ | H | 362 |
| 525 | 2-COO—(CH$_2$)$_2$N(CH$_3$)$_3$ | H | 356 |

EXAMPLE 6

With stirring, 5.1 g of the compound of the formula

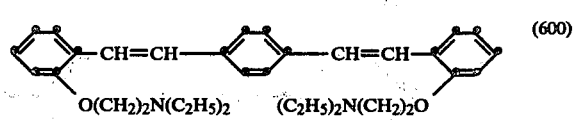
(600)

are heated in 10 ml of trimethylphosphate for 60 minutes to 100° C. After this time, a sample of the reaction mixture forms a clear solution in water. The reaction mixture is diluted with 30 ml of methyl ethyl ketone, cooled, and the crystallised product is filtered with suction and washed repreatedly with methyl ethyl ketone. The residue is dried in vacuo at 100° C., affording 5.1 g of compound of the formula

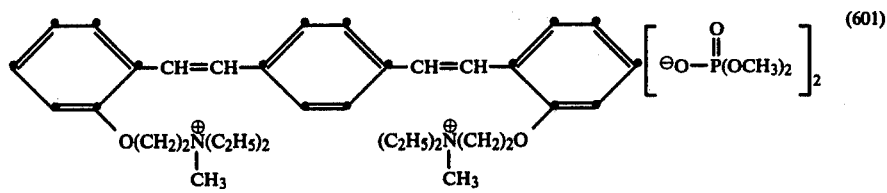

in the form of pale yellow crystals with a melting point of 187° C. The solubility of this product in water at room temperature is over 50%.

The compound of the formula

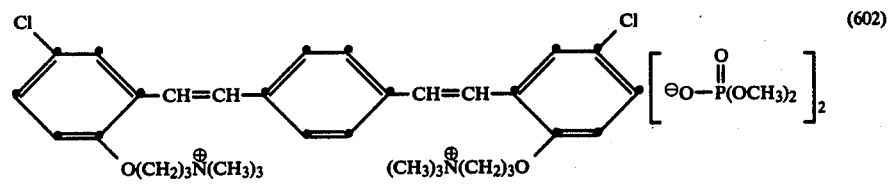

(m.p. 250° C.) is obtained in analogous manner. The solubility of this product in water at room temperature is over 50%, compared with 16% for the corresponding methosulfate.

The fluorescent whitening agents of the formula

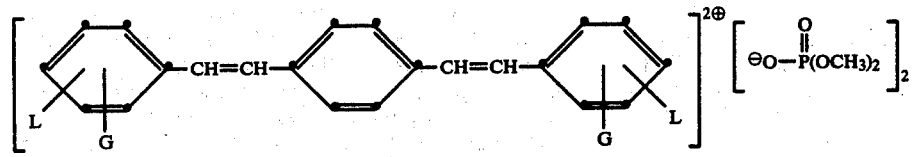

listed in Table V are obtained in a manner similar to that described in the foregoing Examples.

TABLE V

| Formula | G | L | $\lambda_{max}$ in dimethyl formamide (nm) |
|---|---|---|---|
| 603 | 2-O—(CH$_2$)$_3$—N(CH$_3$)$_3$ | H | 367 |
| 604 | 2-O—(CH$_2$)$_2$—N(CH$_3$)$_3$ | H | 367 |
| 605 | 2-O(CH$_2$)$_2$—N⟨piperidine⟩CH$_3$ | H | 367 |
| 606 | 2-O(CH$_2$)$_2$—N⟨morpholine⟩CH$_3$ | H | 364 |
| 607 | 2-O(CH$_2$)$_2$—N⟨pyrrolidine⟩CH$_3$ | H | 367 |
| 608 | 3-O(CH$_2$)$_3$—N(C$_2$H$_5$)$_2$ CH$_3$ | H | 358 |

TABLE V-continued

| Formula | G | L | $\lambda_{max}$ in dimethyl formamide (nm) |
|---|---|---|---|
| 609 | 4-O(CH$_2$)$_2$—N(C$_2$H$_5$)$_2$ CH$_3$ | H | 367 |
| 610 | 2-O—(CH$_2$)$_3$N(CH$_3$)$_3$ | 3-OCH$_3$ | 360 |
| 611 | 2-O(CH$_2$)$_3$—N(CH$_3$)$_3$ | 5-CH$_3$ | 372 |
| 612 | 3-SO$_2$NH(CH$_2$)$_3$—N(CH$_3$)$_3$ | 4-Cl | 366 |
| 613 | 2-SO$_2$NH(CH$_2$)$_3$—N(CH$_3$)$_3$ | H | 353 |
| 614 | 3-CONH(CH$_2$)$_3$—N(CH$_3$)$_3$ | 6-CH$_3$ | 367 |
| 615 | 2-CH$_2$N(CH$_3$)$_3$ | H | 352 |

EXAMPLE 7

With stirring, 6.25 g of the compound of the formula

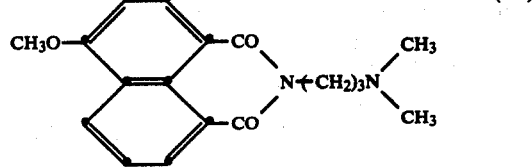

are heated in 5.6 g of trimethylphosphate for 5 minutes to 80° C. After this time, a sample forms a clear solution in water and a dense precipitate of the reaction product forms. The reaction mixture is diluted with 50 ml of methyl ethyl ketone, cooled, and filtered. The residue, which deliquesces in air, is washed repeatedly with methyl ethyl ketone and dried immediately in vacuo at 100° C., affording 8.8 g of compound of the formula

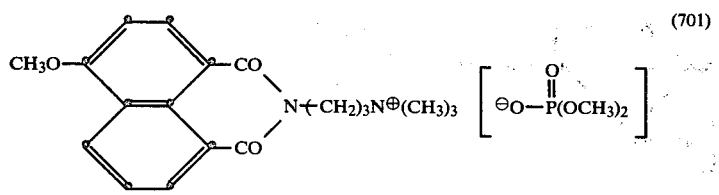 (701)

with a melting point of 188° C. The solubility of this product in water at room temperature is over 60%, compared with 44% for the corresponding salt of phosphoric acid.

The compound of the formula

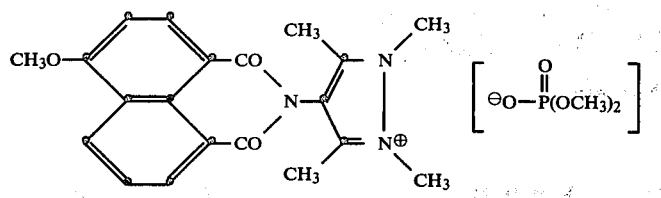

which is used, without isolation, after dilution with water, is obtained in a manner similar to that described in the foregoing Examples. (UV $\lambda_{max}$ 365 nm in DMF).

EXAMPLE 8

Polyacrylonitrile fabric (Orlon 75) is treated in a dyeing machine, at a liquor ratio of 1:20, with an aqueous bath which contains 0.1% of the fluorescent whitening agent of the formula (101), (201), (203), (301), (302), (303), (401), (402), (403), (501), (502), (503), (506), (601) or (612), based on the weight of the goods, 1 g/l of an adduct of 35 moles of ethylene oxide and 1 mole of stearyl alcohol, and 1.5 ml/l of 85% formic acid. The application is effected in accordance with the following temperature programme:

40°–97° C./30 minutes
97° C./30 minutes
97°–40° C./15 minutes.

The polyacrylonitrile fabric is then rinsed for 30 seconds in running softened water and dried at 70° C. in a drying oven. A good white effect is obtained on the treated fabric.

EXAMPLE 9

Modified polyacrylonitrile fabric (Courtelle) is treated in a dyeing machine, at a liquor ratio of 1:20, with an aqueous bath which contains 0.1% of the fluorescent whitening agent of the formula (101), (201), (203), (301) to (303), (401), (402), (403), (405) to (407),(501), (502), (503), (506), (601) or (612), based on the weight of the goods, 1 g/l of oxalic acid, 0.25 g/l of a polyphosphate as chelating agent, and 0.125 g/l of sodium metabisulfite. The application is effected in accordance with the following temperature programme:

40°–97° C./30 minutes
97° C./30 minutes
97°–40° C./15 minutes

The polyacrylonitrile fabric is then rinsed for 30 seconds in running softened water and dried at 70° C. in a drying oven. A good white effect is obtained on the treated fabric.

EXAMPLE 10

Freshly spun, stretched polyacrylonitrile wet tow (corresponding to 3 g dry weight) is immersed, while still moist, at 45° C. for 4 seconds in 100 ml of an aqueous liquor which contains 0.0005% of a fluorescent whitening agent of the formula (101), (301), (401), (402), (403), (501), (506) or (601), and which has been adjusted with concentrated oxalic acid solution to pH 4. The wet tow is then rinsed briefly with water and dried at 90°–100° C. A good white effect is obtained on the polyacrylonitrile fibre. The whitening can also be carried out e.g. at pH 6 (adjustment by addition of sodium acetate). Raising the temperature of the liquor e.g. to 40° C. increases the rate of exhaustion. Stronger white effects are obtained by increasing the concentration of fluorescent whitening agent to e.g. 0.005%.

EXAMPLE 11

A bleached cotton fabric is treated in a dyeing machine, at a liquor ratio of 1:20, with an aqueous bath which contains 0.1% of the fluorescent whitening agent of the formula (501), (502), (503), (506), (601) or (612), based on the weight of the cotton, and 5 g/l of sodium sulfate. The application is effected in accordance with the following temperature programme:

20°–50° C./15 minutes
50° C./15 minutes.

The cotton fabric is then rinsed for 20 seconds in running sofened water and dried at 70° C. in a drying oven. A good white effect is obtained on the treated cotton.

EXAMPLE 12

Bleached cotton fabric is padded at room temperature with an aqueous liquor which contains 1 g/l of the fluorescent whitening agent of the formula (501), (502), (503), (506) or (601). The pick-up is 75%. The cotton is then dried for 30 seconds at 130° C. in a thermofixing machine. A good white effect is obtained on the treated cotton fabric.

EXAMPLE 13

A concentrated liquid detergent is prepared by mixing the following components:

| | % by weight |
|---|---|
| ethoxylated alcohols (C₁₂–C₁₃ alcohol with 6.5 moles of ethylene oxide) | 60.0 |
| 1-methyl-1-oleylamidoethyl-2-oleyl-imidazolinium methosulfate | 26.7 |
| compound of the formula (501), (502), (601) or (612) | 0.3 |
| water | 12.0 |
| customary additives | 1.0 |

2 kg of bleached cotton fabric are washed for 10 minutes at 50° C. in 60 liters of water of 100 ppm hardness which contains 50 to 60 g of the above detergent. After rinsing and drying, the fabric has a strong white effect and a soft handle.

Similar results are obtained by using non-crosslinked di-tallow dimethylammonium chloride instead of the above imidazolinium compound.

EXAMPLE 14

Bleached cotton fabric is washed at a liquor ratio of 1:20 for 15 minutes in a warm aqueous liquor of 40° C. which contains, per liter, 0.5 g of an adduct of 10 moles of ethylene oxide and 1 mole of stearyl alcohol, and 0.01 g of the fluorescent whitening agent of the formula (501), (502), (503), (505) or (601). The cotton is then rinsed for 20 seconds in running drinking water and dried at 70° C. in a drying oven. A good white effect is obtained on the treated cotton fabric.

EXAMPLE 15

Polyamide 66 woven jersey is treated in a dyeing machine, at a liquor ratio of 1:20, with an aqueous bath which contains 0.1% of the fluorescent whitening agent of the formula (401) to (403) or (405) to (407), based on the weight of the fabric, and 3 g/l of sodium dithionite, stabilised with 40% sodium pyrophosphate. The application is effected in accordance with the following temperature programme:

40°–97° C./30 minutes
97° C./30 minutes
97°–40° C./15 minutes.

The polyamide fabric is then rinsed for 30 seconds in flowing softened water and dried at 70° C. in a drying oven. A good white effect is obtained on the treated fabric.

What is claimed is:

1. A fluorescent whitening composition which is an aqueous solution of 1 to 60% by weight, based on the weight of the solution, of a cationic fluorescent whitening agent of the formula

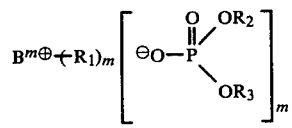

wherein
B is a fluorescent whitening agent selected from the group consisting of 2-furanylbenzimidazoles, 2-azolylbenzimidazoles, 2-stilbenylbenzimidazoles and 2,5-(benzimidazolyl)furanes,
m is the number of basic amino groups, and each of $R_1$, $R_2$ and $R_3$ is alkyl of 1 to 4 carbon atoms which is unsubstituted or substituted by a non-chromophoric group, or is alkenyl of 2 to 4 carbon atoms which is unsubstituted or substituted by a non-chromophoric group.

2. The fluorescent whitening composition of claim 1 wherein
m is 1 or 2, $R_2$ and $R_3$ are identical, each of $R_1$ $R_2$ and $R_3$ is alkyl of 1 to 4 carbon atoms, alkenyl of 2 to 4 carbon atoms, or benzyl, and
B is a fluorescent whitening agent of the formula

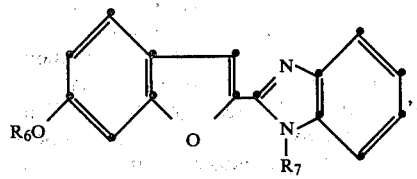

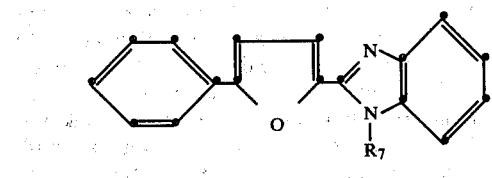

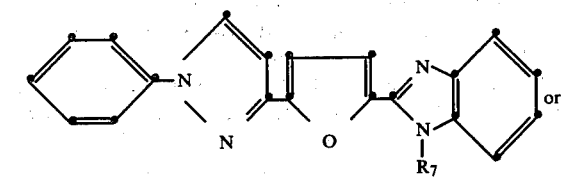

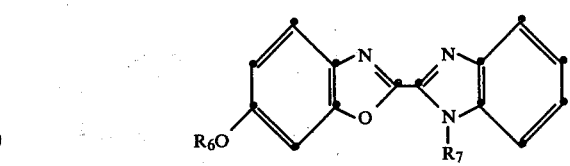

wherein
each of $R_6$ and $R_7$ independently is alkyl of 1 to 6 carbon atoms which is unsubstituted or substituted by a non-chromophoric group, alkenyl of 2 to 6 carbon atoms which is unsubstituted or substituted by a non-chromophoric group, or is phenyl, and wherein the benzene rings and the heterocyclic rings can also carry non-chromophoric substituents.

3. The fluorescent whitening composition of claim 2 wherein
$R_1$, $R_2$ and $R_3$ are identical and are alkyl of 1 to 3 carbon atoms and B is a fluorescent whitening agent radical of the formula

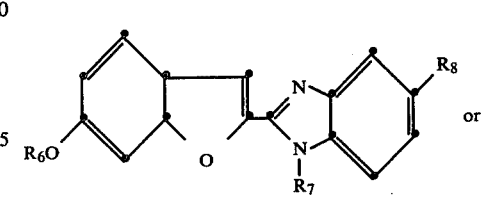

-continued

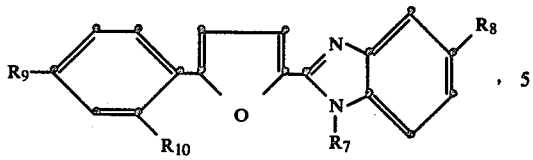, 5

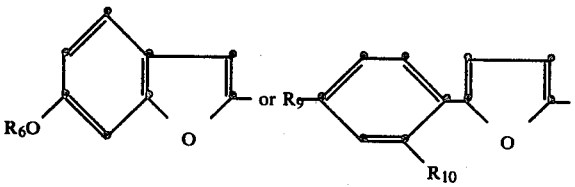

wherein
$R_6$ is alkyl of 1 to 4 carbon atoms,
$R_7$ is alkyl of 1 to 4 carbon atoms, benzyl, phenyl, alkenyl of 3 to 4 carbon atoms, cyanolalkyl of 2 to 3 carbon atoms, or alkoxycarbonylmethyl containing 1 to 3 carbon atoms in the alkoxy moiety,
$R_8$ is hydrogen, methyl, chlorine, alkylsulfonyl of 1 to 4 carbon atoms, phenylsulfonyl, cyano, trifluoromethyl, phenoxysulfonyl, alkoxycarbonyl containing a total of 2 to 5 carbon atoms, carboxyl, —$CONZ_1Z_2$ or —$SO_2NZ_1Z_2$, wherein $Z_1$ is hydrogen, alkyl of 1 to 4 carbon atoms, alkenyl of 3 to 4 carbon atoms, hydroxyalkyl of 2 to 4 carbon atoms, alkoxyalkyl containing a total of 3 to 6 carbon atoms, or benzyl, and $Z_2$ is hydrogen, alkyl of 1 to 4 carbon atoms, or $Z_1$ and $Z_2$, together with the nitrogen atom to which they are attached, can also form a morpholine ring, and
$R_9$ and $R_{10}$, each independently of the other, are hydrogen, chlorine or methyl.

4. The fluorescent whitening composition of claim 3 wherein the fluorescent whitening agent is of the formula

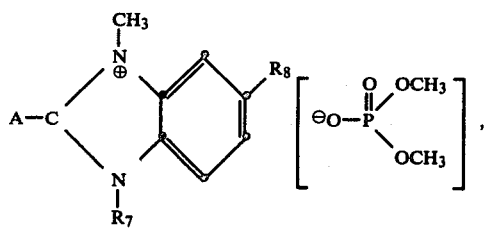

wherein A is a radical of the formula wherein
$R_6$ is alkyl of 1 to 4 carbon atoms and each of $R_9$ and $R_{10}$ independently is hydrogen, chlorine or methyl,
$R_7$ is alkyl of 1 to 4 carbon atoms, benzyl, phenyl, alkenyl of 3 or 4 carbon atoms, cyanoalkyl of 2 or 3 carbon atoms, alkoxycarbonylmethyl containing 1 to 3 carbon atoms in the alkoxy moiety, and $R_8$ is hydrogen, methyl, chlorine, alkylsulfonyl of 1 to 4 carbon atoms, phenylsulfonyl, cyano, trifluoromethyl, phenoxysulfonyl, alkoxycarbonyl containing a total of 2 to 5 carbon atoms, carboxyl, $CONZ_1Z_2$ or $SO_2NZ_1Z_2$, wherein $Z_1$ is hydrogen, alkyl of 1 to 4 carbon atoms, alkenyl of 3 or 4 carbon atoms, hydroxyalkyl of 2 to 4 carbon atoms, alkoxyalkyl containing a total of 3 to 6 carbon atoms, or benzyl, and $Z_2$ is hydrogen, alkyl of 1 to 4 carbon atoms, or $Z_1$ and $Z_2$, together with the nitrogen atom to which they are attached, can also form a morpholine ring.

5. The fluorescent whitening composition of claim 4 wherein
$R_6$ is methyl,
$R_7$ is alkyl of 1 to 4 carbon atoms, benzyl, phenyl or cyanoalkyl of 2 or 3 carbon atoms,
$R_8$ is hydrogen, alkylsulfonyl of 1 to 4 carbon atoms, phenylsulfonyl, phenoxysulfonyl, sulfamoyl, alkylsulfamoyl of 1 to 4 carbon atoms, alkoxycarbonyl of 2 to 4 carbon atoms, cyano or chlorine, $R_9$ is chlorine and $R_{10}$ is hydrogen, chlorine or methyl.

6. The fluorescent whitening composition of claim 1 further containing an excess of a water-soluble trialkylphosphate or trialkenylphosphate.

7. The fluorescent whitening composition of claim 1 further containing a buffering agent.

* * * * *

UNITED STATES PATENT AND TRADEMARK OFFICE
CERTIFICATE OF CORRECTION

PATENT NO. : 4,432,886
DATED : February 21, 1984
INVENTOR(S) : Hans K. Meyer

It is certified that error appears in the above-identified patent and that said Letters Patent are hereby corrected as shown below:

Claim 4, column 31, first formula to the left reads

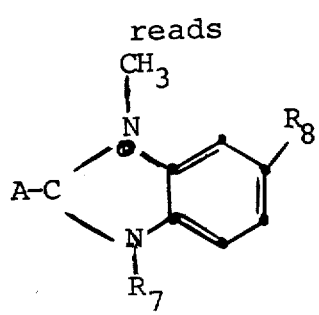

should read

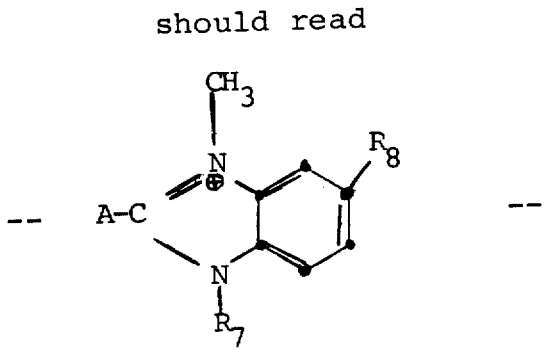

Signed and Sealed this

Twenty-fifth Day of September 1984

[SEAL]

Attest:

GERALD J. MOSSINGHOFF

Attesting Officer

Commissioner of Patents and Trademarks